(12) United States Patent
Booth et al.

(10) Patent No.: US 8,436,167 B2
(45) Date of Patent: May 7, 2013

(54) CHEMICAL COMPOUNDS

(75) Inventors: Rebecca Jane Booth, Macclesfield (GB); Peter Anthony Cittern, Bristol (GB); Jeffrey Norman Crabb, Bristol (GB); John Horbury, Bristol (GB); David Wyn Calvert Jones, Bristol (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 13/038,245

(22) Filed: Mar. 1, 2011

(65) Prior Publication Data

US 2012/0059022 A1    Mar. 8, 2012

Related U.S. Application Data

(63) Continuation of application No. 12/615,935, filed on Nov. 10, 2009, now abandoned, which is a continuation of application No. 10/571,254, filed as application No. PCT/GB2004/003829 on Sep. 8, 2004, now abandoned.

(30) Foreign Application Priority Data

Sep. 10, 2003  (GB) ................................ 03211237.3
Mar. 4, 2004   (GB) ................................ 0404859.1

(51) Int. Cl.
    *C07D 239/36*  (2006.01)
    *C07D 239/42*  (2006.01)

(52) U.S. Cl.
    USPC ........................... 544/332; 544/330; 544/331

(58) Field of Classification Search .................. 544/332, 544/330
    See application file for complete search history.

(56) References Cited

U.S. PATENT DOCUMENTS

| | | | |
|---|---|---|---|
| 4,645,858 A | 2/1987 | Lowrie et al. | |
| 4,970,313 A | 11/1990 | Wess et al. | |
| 4,977,279 A | 12/1990 | Wess et al. | |
| 5,026,698 A | 6/1991 | Fujikawa et al. | |
| 5,278,313 A | 1/1994 | Thottathil et al. | |
| 5,399,722 A | 3/1995 | Beck et al. | |
| 5,594,153 A | 1/1997 | Thottathil et al. | |
| 6,278,001 B1 | 8/2001 | Solladie et al. | |
| 6,331,641 B1 | 12/2001 | Taoka et al. | |
| 6,784,171 B2 | 8/2004 | Taylor et al. | |
| 6,844,437 B1 | 1/2005 | Taylor et al. | |
| 6,870,059 B2 | 3/2005 | Kooistra et al. | |
| 6,875,867 B2 | 4/2005 | Brodfuehrer et al. | |
| 7,157,255 B2 | 1/2007 | Blacker et al. | |
| 7,304,156 B2 | 12/2007 | Matsushita et al. | |
| 7,416,865 B2 | 8/2008 | Blacker et al. | |
| 7,442,811 B2 | 10/2008 | Bakel Van et al. | |
| 7,511,140 B2 | 3/2009 | Horbury et al. | |
| 7,524,955 B2 | 4/2009 | Newton et al. | |
| 7,642,363 B2 | 1/2010 | Kooistra et al. | |
| 2003/0018199 A1 | 1/2003 | Brodfuehrer et al. | |
| 2003/0114685 A1 | 6/2003 | Niddam-Hildesheim et al. | |
| 2005/0090674 A1 | 4/2005 | Hof | |
| 2005/0124639 A1 | 6/2005 | Joshi et al. | |
| 2005/0209259 A1 | 9/2005 | Huang | |
| 2006/0004200 A1 | 1/2006 | Gudipati et al. | |
| 2006/0293355 A1 | 12/2006 | Booth et al. | |
| 2007/0105882 A1 | 5/2007 | Black et al. | |
| 2007/0255060 A1 | 11/2007 | Okada et al. | |
| 2008/0058520 A1 | 3/2008 | Matsushita et al. | |
| 2008/0188657 A1 | 8/2008 | Lenger | |
| 2008/0207903 A1 | 8/2008 | Butters et al. | |
| 2008/0221323 A1 | 9/2008 | Crabb et al. | |
| 2008/0280336 A1 | 11/2008 | Blacker et al. | |
| 2009/0264654 A1 | 10/2009 | Newton et al. | |
| 2009/0286819 A1 | 11/2009 | Horbury et al. | |

FOREIGN PATENT DOCUMENTS

| | | |
|---|---|---|
| CA | 2545316 | 5/2005 |
| EP | 0521471 | 10/2000 |
| WO | WO 90/03973 | 4/1990 |
| WO | WO 93/08823 | 5/1993 |
| WO | WO 97/03959 | 2/1997 |
| WO | WO 97/19917 | 6/1997 |
| WO | WO 97/49681 | 12/1997 |
| WO | WO 00/32189 | 6/2000 |
| WO | WO 00/42024 | 7/2000 |
| WO | WO 00/49014 | 8/2000 |
| WO | WO 01/22962 | 4/2001 |
| WO | WO 01/36384 | 5/2001 |
| WO | WO 01/54669 | 8/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/06266 | 1/2002 |
| WO | WO 02/30415 | 4/2002 |
| WO | WO 02/43667 | 6/2002 |

(Continued)

OTHER PUBLICATIONS

Hiyama et al. "Synthesis of Artificial HMG-CoA Reductase Inhibitors Based on the Olefination Strategy" Bull. Chem. Soc. Jpn. 68 (1):364-372 (1995).

Iida et al. "PPARγ ligands, troglitazone and pioglitazone, up-regulate expression of HMG-CoA synthase and HMG-CoA reductase gene in THP-1 macrophages" FEBS Letters 520(1): 177-181 (2002).

Kaneko et al. "Preparation of optically active 5,6-epoxyhexanoic acid esters as materials for physiologically active substances" Chemical Abstracts + Indexes, American Chemical Society, Columbus, US 118(11):832 (1993).

Khan et al. "A Prospective, Randomized Comparison of the Metabolic Effects of Pioglitazone or Rosiglitazone in Patients With Type 2 Diabetes Who Were Previously Treated With Troglitazone" Diabetes Care 25(4): 708-711 (2002).

(Continued)

*Primary Examiner* — Venkataraman Balasubramanian
(74) *Attorney, Agent, or Firm* — Morgan, Lewis & Bockius LLP

(57) ABSTRACT

Two polymorphic forms of bis[(E)-7-[4-(4-fluorophenyl)-6-isopropyl-2-[methyl(methylsulfonyl)amino]pyrimidin-5-yl] (3R,5S)-3,5-dihydroxyhept-6-enoic acid] calcium salt, processes for making them and their use as HMG Co-A reductase inhibitors are described.

18 Claims, 6 Drawing Sheets

FOREIGN PATENT DOCUMENTS

| | | |
|---|---|---|
| WO | WO 02/43732 | 6/2002 |
| WO | WO 02/072566 | 9/2002 |
| WO | WO 02/083637 | 10/2002 |
| WO | WO 02/098854 | 12/2002 |
| WO | WO 03/006439 | 1/2003 |
| WO | WO 03/016317 | 2/2003 |
| WO | WO 03/018555 | 3/2003 |
| WO | WO 03/026573 | 4/2003 |
| WO | WO 03/026659 | 4/2003 |
| WO | WO 03/059901 | 7/2003 |
| WO | WO 03/087112 | 10/2003 |
| WO | WO 03/097614 | 11/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/089895 | 10/2004 |
| WO | WO 2004/103977 | 12/2004 |
| WO | WO 2004/108691 | 12/2004 |
| WO | WO 2005/005384 | 1/2005 |
| WO | WO 2005/023778 | 3/2005 |
| WO | WO 2005/023779 | 3/2005 |
| WO | WO 2005/028450 | 3/2005 |
| WO | WO 2005/030215 | 4/2005 |
| WO | WO 2005/040134 | 5/2005 |
| WO | WO 2005/042522 | 5/2005 |
| WO | WO 2005/047276 | 5/2005 |
| WO | WO 2005/051921 | 6/2005 |
| WO | WO 2005/054207 | 6/2005 |
| WO | WO 2005/056534 | 6/2005 |
| WO | WO 2005/063728 | 7/2005 |
| WO | WO 2005/068435 | 7/2005 |
| WO | WO 2005/077916 | 8/2005 |
| WO | WO 2005/077917 | 8/2005 |
| WO | WO 2005/092867 | 10/2005 |
| WO | WO 2006/017357 | 2/2006 |
| WO | WO 2006/035277 | 4/2006 |
| WO | WO 2006/067456 | 6/2006 |
| WO | WO 2006/079611 | 8/2006 |
| WO | WO 2006/089401 | 8/2006 |
| WO | WO 2007/007119 | 1/2007 |

OTHER PUBLICATIONS

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,-Diketo Esters Derived From Tartaric Acid. A Facile Route to Optically Active 6-oxo-3,5-syn-isopropylidenedioxyhexanoate, a Versatile Synthetic Intermediate of Artificial HMG Co-A Reductase Inhibitors" Tetrahedron Letters 34(3):513-516 (1993).

Moore et al. "Biosynthesis of the hypocholesterolemic agent mevinolin by *Aspergillus terreus*. Determination of the origin of carbon, hydrogen, and oxygen atoms by carbon-13 NMR and mass spectrometry" J. Am. Chem. Soc. 107(12): 3694-3701 (1985).

Nezasa et al. "Pharmacokinetics and disposition of rosuvastatin, a new 3-hydroxy-3-methylglutaryl coenzyme A reductase inhibitor, in rat" Xenobiotica 32(8):715-727 (2002).

Prasad et al. "A novel diastereroselective synthesis of lactone moiety of compactin" Tetrahedron Letters 25(23):2435-2438 (1984).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Rutishauser "The role of statins in clinical medicine—LDL—cholesterol lowering and beyond" Swiss Medical Weekly 136: 41-49 (2006).

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Simone "Oncology: Introduction" Cecil Textbook of Medicine, Edited by Bennett, 20th Edition, vol. 1: 1004-1010 (1996).

Solladié et al. "Chrial Sulfoxides in Asymmetric Synthesis: Enantioselective Synthesis of the Lactonic Moiety of (+)-Compactin and (+)-Mevinolin. Application of a Compactin Analogue" J. Org. Chem. 60:7774-7777 (1995).

Watanabe et al. "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors" Bioorganic & Medicinal Chemistry 5(2):437-444 (1997).

Wess et al. "Stereoselective Synthesis of HR 780 A New Highly Potent HMG-CoA Reductase Inhibitor", Tetrahedron Letters 31(18): 2545-2548 (1990).

Remington Farmacia published Dec. 12, 2000 cited by Colombian Patent Office in the corresponding Colombian patent application (Translation of Colombian Patent Examiner's comments in regards to this publication: "Remington Farmacia teaches that polymorphism is a property broadly disclosed in the compounds of pharmaceutical interest and that is duty of the pre-formulator to find all the polymorphic forms of a compound to reach an acceptable raw material, as the polymorphs have different physical properties.").

Jikkenn Kagaku Koza 1, Kihon Sosa I, 4th Edition, pp. 184-186, compiled by the Chemical Society of Japan, published on Nov. 5, 1990, Maruzen Co.

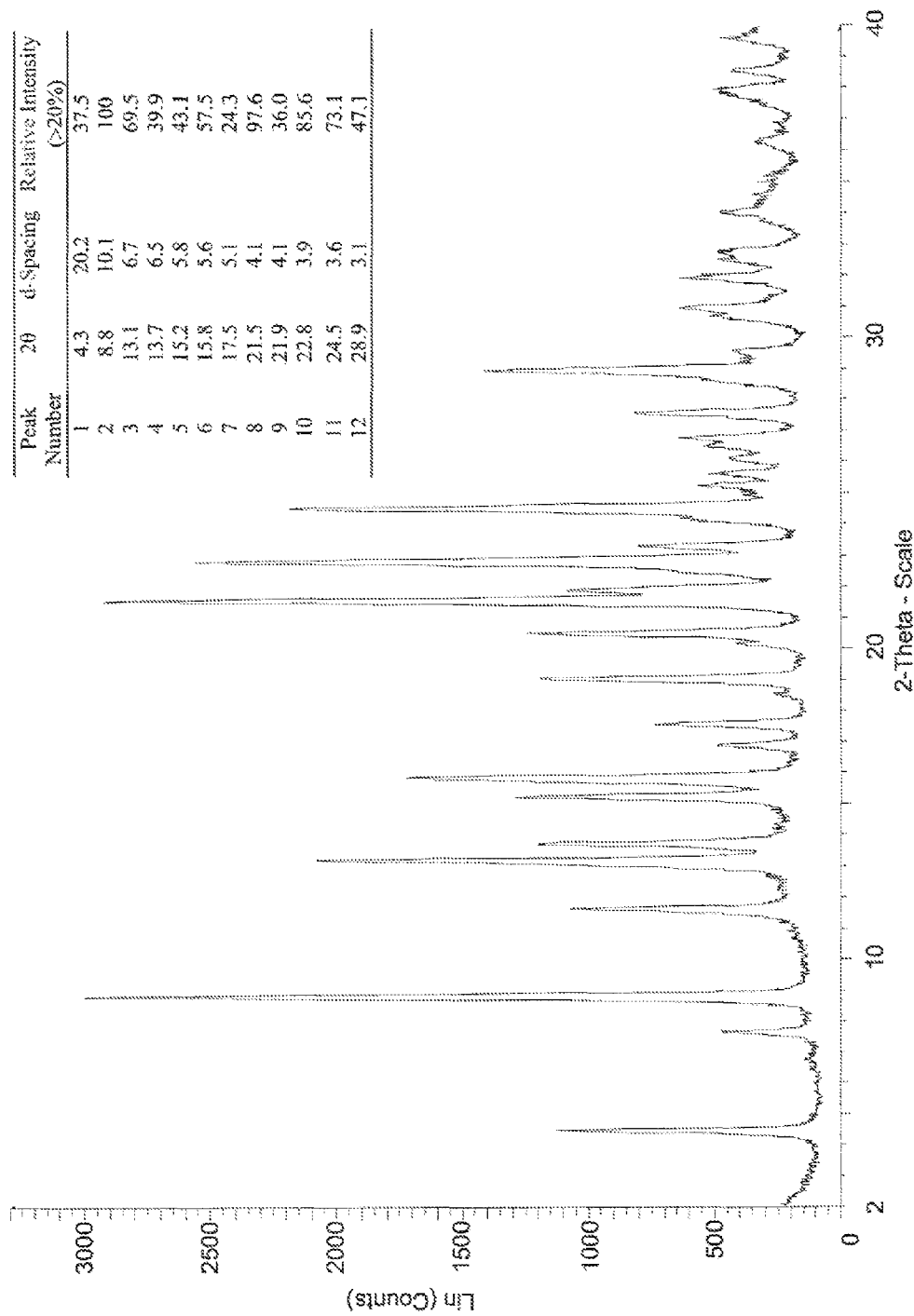
Figure 1A: XRD spectra of a typical sample of Form B

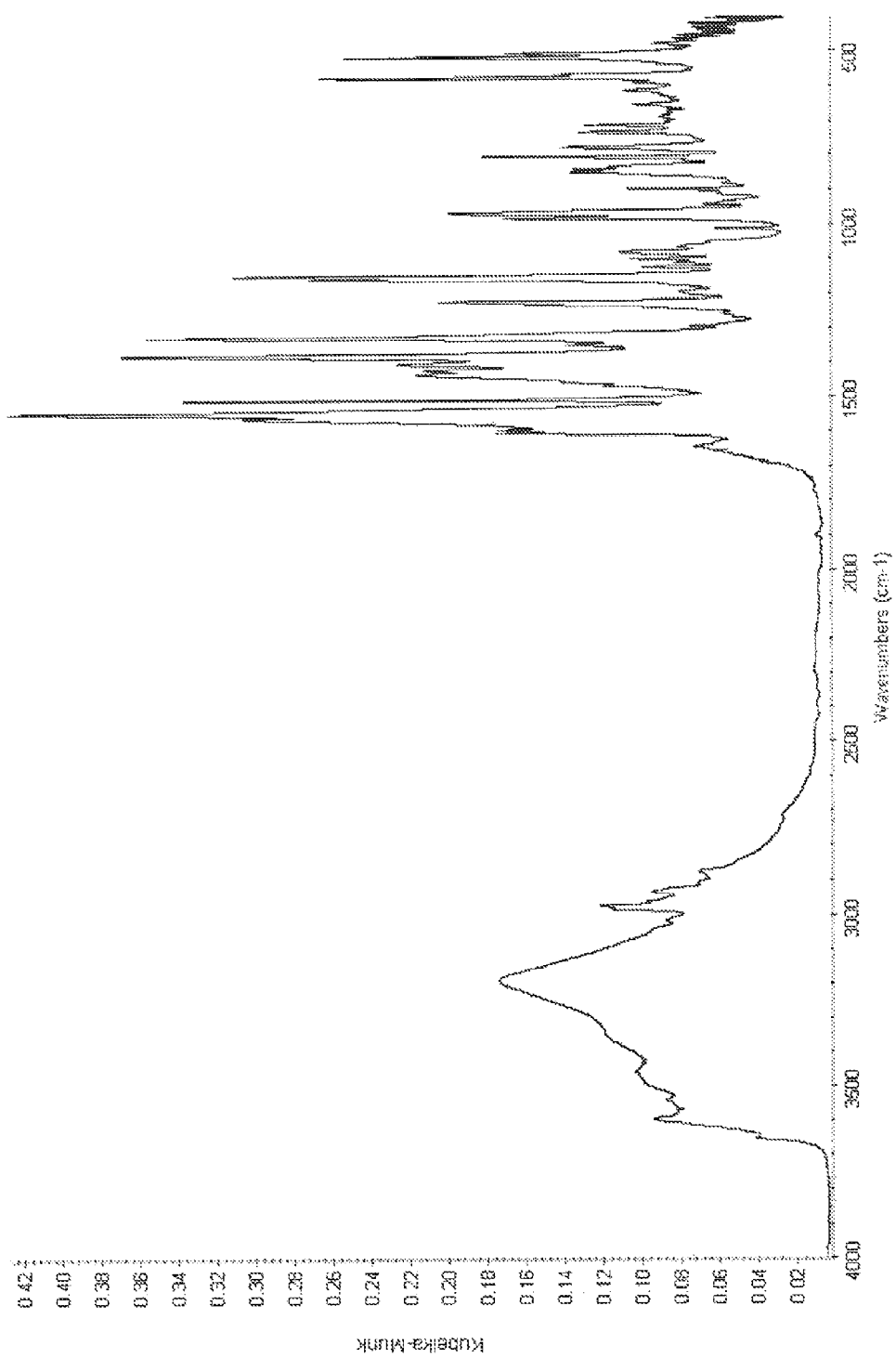

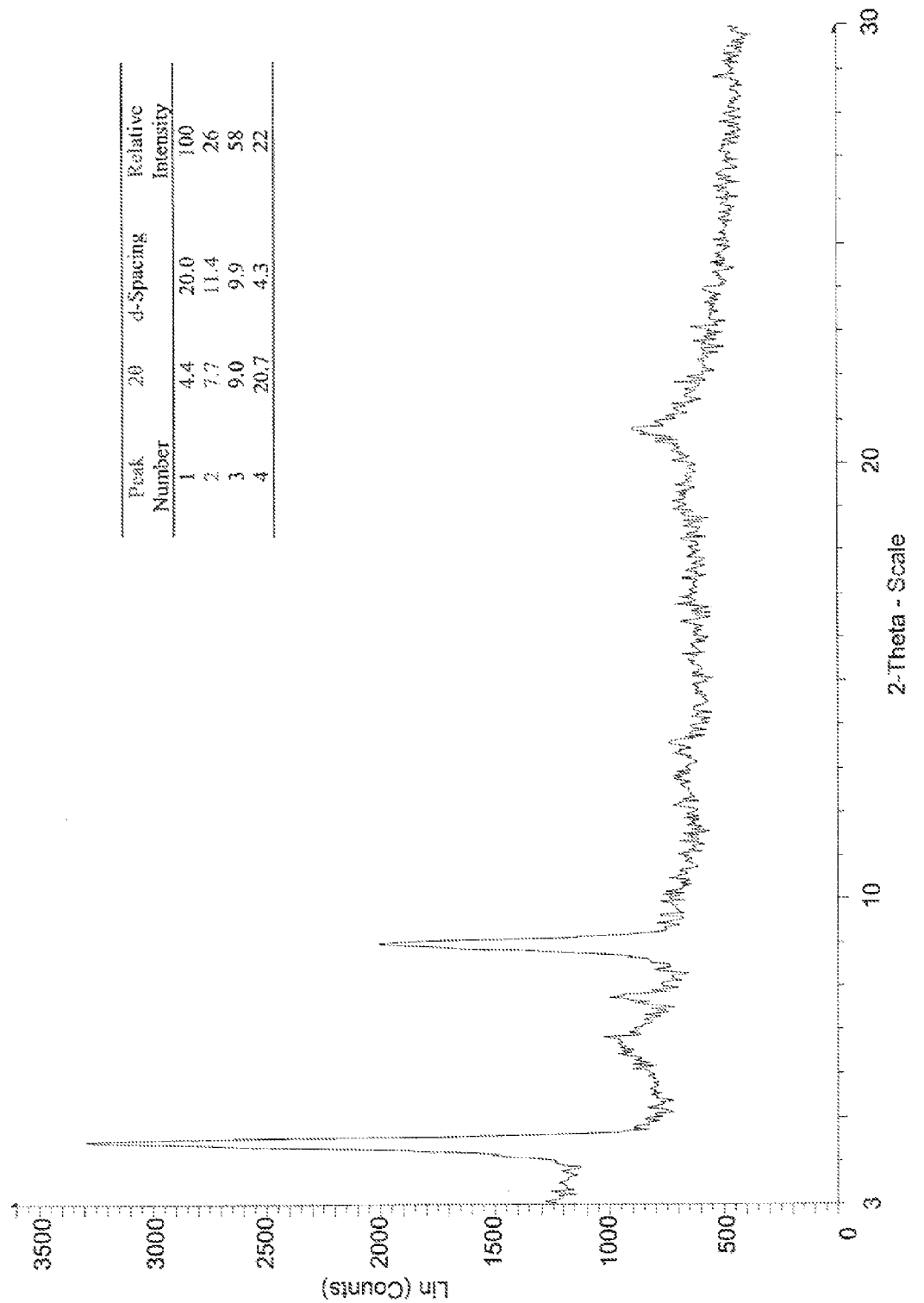
Figure 2A: XRD trace of a sample of Form B-1

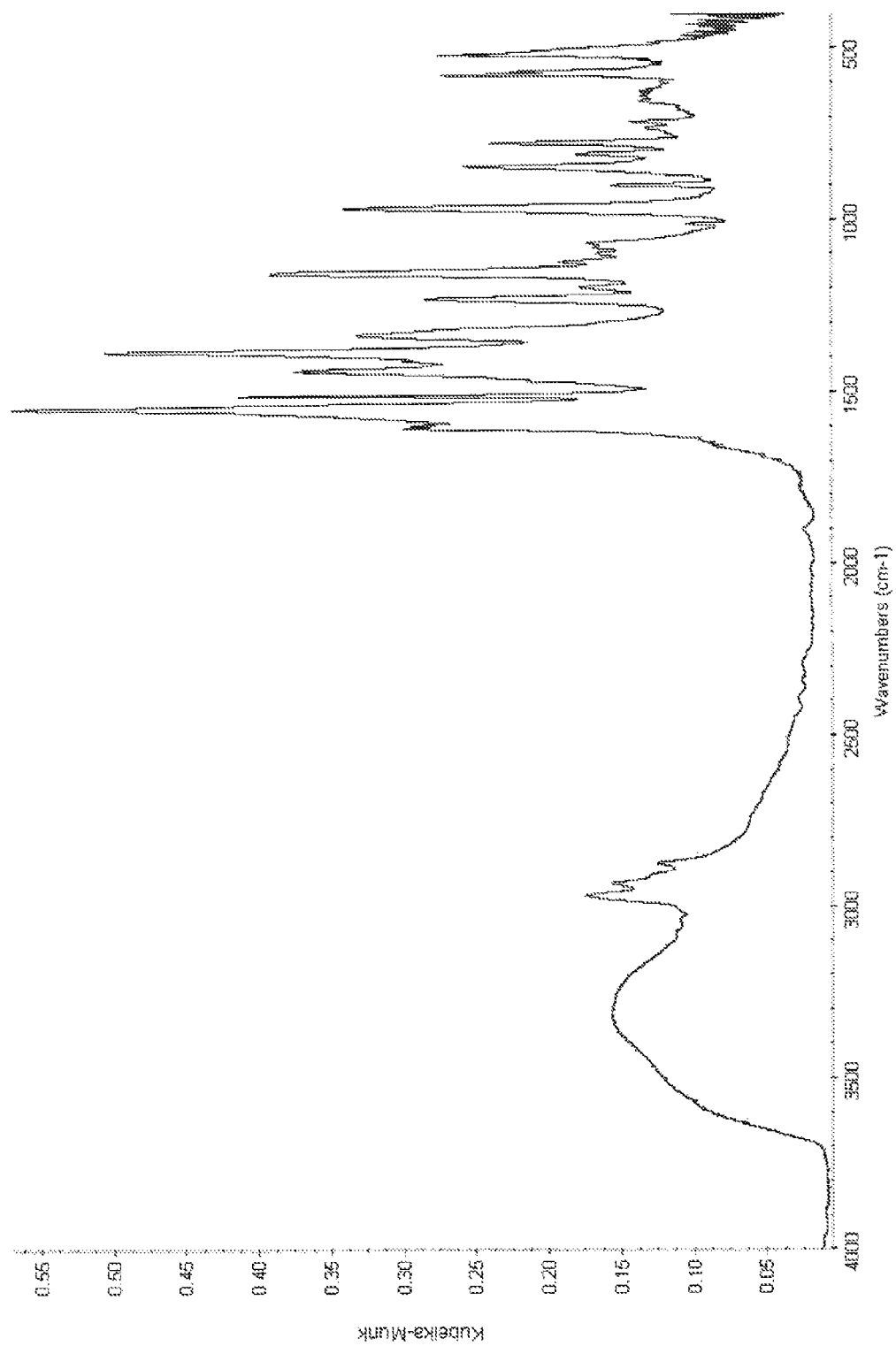

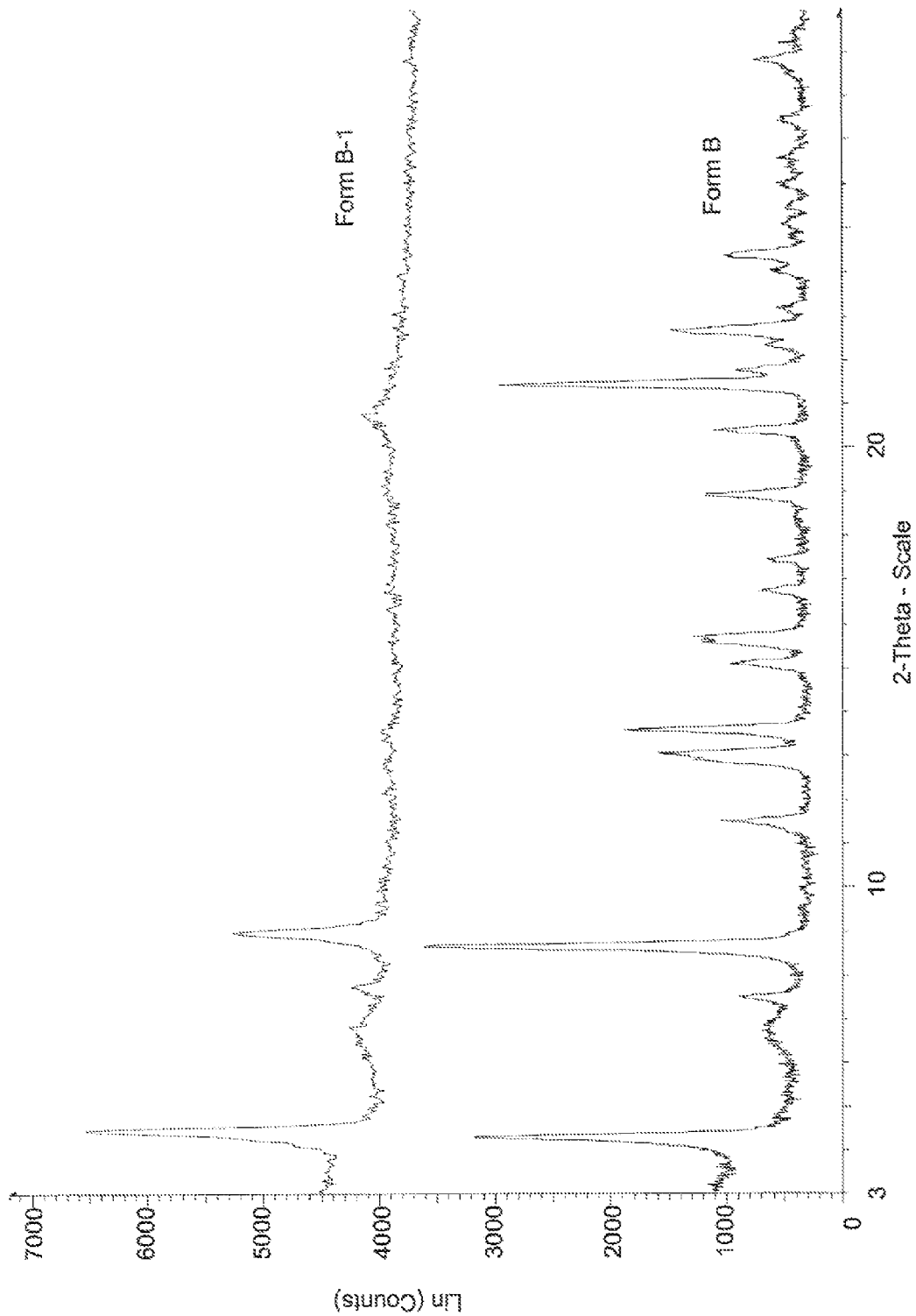

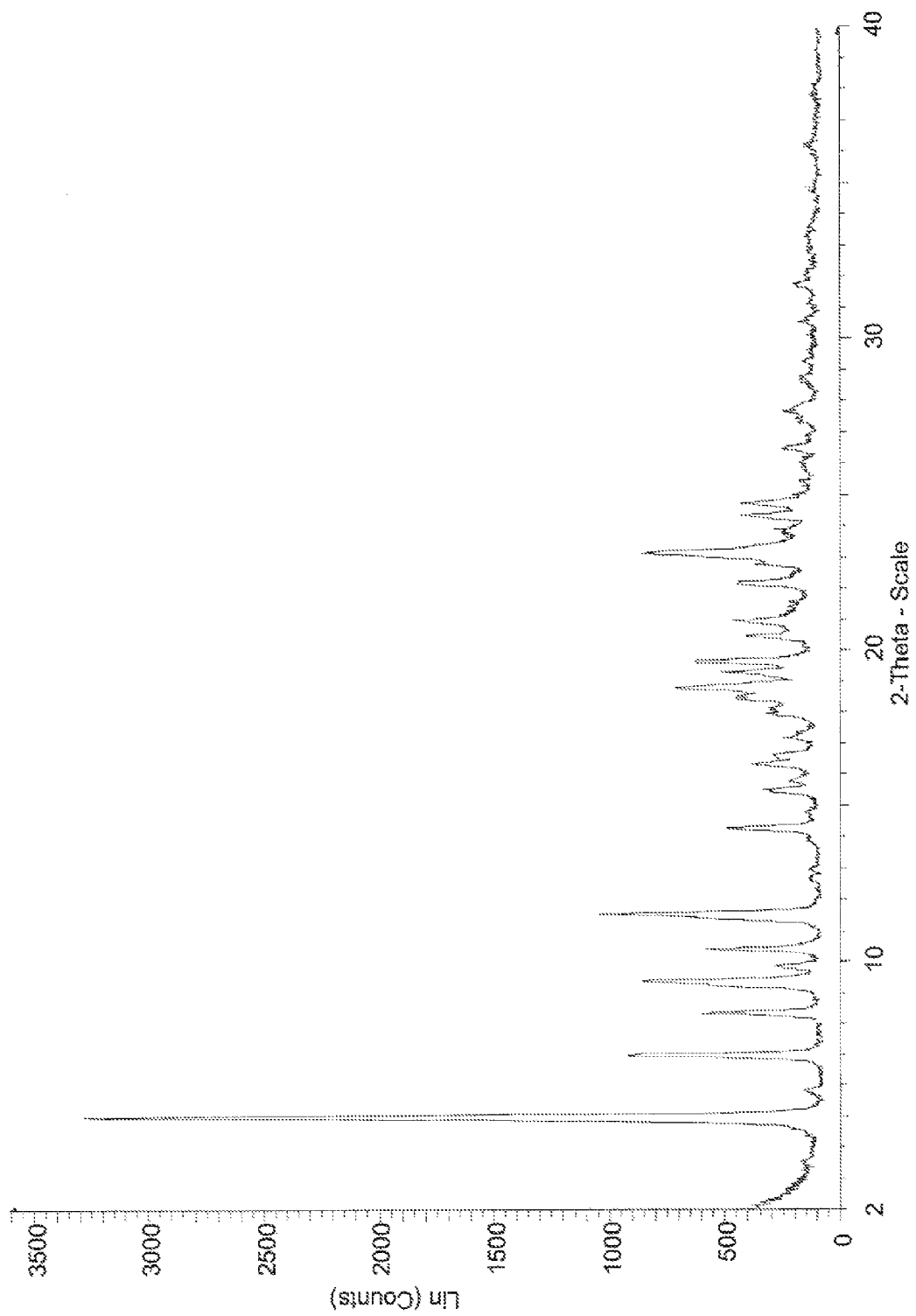
Figure 4: XRD pattern for Form A

CHEMICAL COMPOUNDS

This application is a continuation application of U.S. patent application Ser. No. 12/615,935 (filed Nov. 10, 2009, now abandoned) which is a continuation application of U.S. patent application Ser. No. 10/571,254 (filed Mar. 9, 2006, now abandoned), which is a U.S. National Phase Application of International Application No. PCT/GB04/03829 (filed Sep. 8, 2004), which claims the benefit of British Patent Application No. 0321127.3 (filed Sep. 10, 2003) and British Patent Application No. 0404859.1 (filed Mar. 4, 2004), all of which are herein incorporated by reference in their entirety.

The present invention relates to a novel crystalline chemical compound and more particularly to a novel crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt, hereinafter referred to as "the Agent", and illustrated in Formula (I) hereinafter, which compound is an inhibitor of the enzyme 3-hydroxy-3-methylglutaryl-coenzyme A reductase (HMG CoA reductase) and is useful as a pharmaceutical agent, for example in the treatment of hyperlipidemia, hypercholesterolemia and atherosclerosis, as well as other diseases or conditions in which HMG CoA reductase is implicated. The invention also relates to processes for the manufacture of the crystalline form, pharmaceutical compositions comprising the crystalline form and the use of the crystalline form in medical treatment.

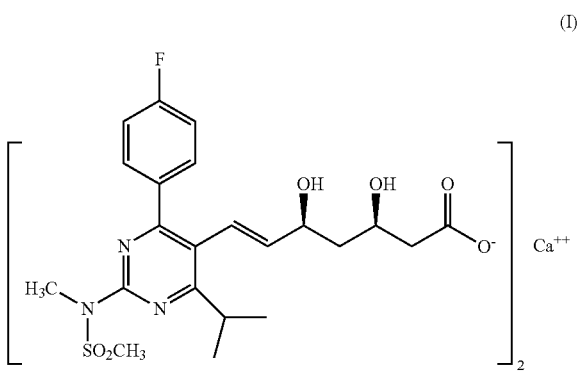

(I)

European Patent Application, Publication No. 521471 (hereinafter EPA 521471), which is herein incorporated by reference, discloses an amorphous (powder) form of the Agent, prepared by dissolving the corresponding sodium salt in water, adding calcium chloride and collecting the resultant precipitate by filtration.

International Patent Application WO 2004/014872 discloses an improved method for the precipitation of the amorphous form of the Agent.

International Patent Application WO 00/42024 discloses a crystalline form of the Agent, referred to as Form A therein, which is prepared from a mixture of water and one or more organic solvents, for example, a 1:1 mixture of acetonitrile and water. However no suitable conditions were found for preparation of Form A from water without the presence of an organic co-solvent. The use of organic solvents in large scale manufacture is generally undesirable for environmental reasons (for example, the disposal of large volumes of waste), and safety reasons (for example, if the product is a pharmaceutical, the need to ensure that organic solvents are removed from the final product). Therefore there is an on-going need to find crystalline forms of the Agent which can be produced from water alone.

We have now surprisingly and unexpectedly discovered that the Agent can be prepared in a second crystalline form from water without the need for an organic co-solvent.

According to the present invention there is provided a crystalline hydrated form of the Agent having an X-ray powder diffraction pattern with peaks at 2-theta (2θ)=8.8, 13.1 and 21.5° (hereinafter referred to as Form B).

According to the present invention there is provided a crystalline hydrated form of the Agent having an X-ray powder diffraction pattern with peaks at 2-theta (2θ)=4.3, 8.8, 13.1, 13.7, 21.5, 22.8 and 28.9°.

According to the present invention there is provided a crystalline hydrated form of the Agent having an X-ray powder diffraction pattern with peaks at 2-theta (2θ)=4.3, 8.8, 13.1, 13.7, 15.2, 15.8, 17.5, 21.5, 21.9, 22.8, 24.5 and 28.9°.

According to the present invention there is provided a crystalline hydrated form of the Agent having an X-ray powder diffraction pattern substantially as shown in FIG. 1A.

BRIEF DESCRIPTION OF DRAWINGS

FIG. 1A shows X-ray powder diffraction spectra of a typical sample of Form B.

FIG. 1B shows DRIFT IR Spectrum of Form B.

FIG. 2A shows X-ray powder diffraction trace of a sample of Form B-1.

FIG. 2B shows DRIFT IR Spectrum of Form B-1.

FIG. 3 shows a comparison of the X-ray powder diffraction traces of Forms B and B-1.

FIG. 4 shows X-ray powder diffraction pattern for Form A.

Form B obtained according to the present invention is substantially free from other crystal and non-crystal forms of the Agent. The term "substantially free from other crystal and non-crystal forms" shall be understood to mean that the desired crystal form contains less than 50%, preferably less than 20%, more preferably less than 10%, more preferably less than 5% of any other forms of the Agent.

The X-ray powder diffraction (referred to herein as XRPD or XRD) spectrum was determined by mounting a sample of the crystalline form on Siemans single silicon crystal (SSC) wafer mounts and spreading out the sample into a thin layer with the aid of a microscope slide. Using a Siemens D5000 diffractometer, the sample was spun at 30 revolutions per minute (to improve counting statistics) and irradiated with X-rays generated by a copper long-fine focus tube operated at 40 kV and 40 mA with a wavelength of 1.5406 angstroms. The collimated x-ray source was passed through an automatic variable divergence slit set at V20 (20 mm path length) and the reflected radiation directed through a 2 mm antiscatter slit and a 0.2 mm detector slit. The sample was exposed for 4 seconds per 0.02 degree 2-theta increment (continuous scan mode) over the range 2 degrees to 40 degrees 2-theta in theta-theta mode. The running time was 2 hours 6 minutes and 40 seconds. The instrument was equipped with a scintillation counter as detector. Control and data capture was by means of a DECpc LPv 433sx personal computer running with Diffrac AT (Socabim) software.

The X-ray powder diffraction spectra of a typical sample of Form B is shown in FIG. 1A hereinafter.

It will be understood that the 2-theta values of the X-ray powder diffraction pattern may vary slightly from one machine to another or from one sample of Form B to another, and so the values quoted are not to be construed as absolute. It will also be understood that the relative intensities of peaks may vary according to the orientation of the sample under test so that the intensities shown in the XRD trace included herein are illustrative and not intended to be used for absolute comparison.

Form B may also be characterised by its infra-red (IR) spectrum, such as that carried out by the DRIFT (Diffuse-Reflectance Infrared Fourier Transform Spectroscopy) technique. A DRIFT spectrum of Form B is shown in Example 1 hereinafter. The spectrum was acquired using 2% w/w (in powdered KBr) over the 4,000-400 cm-1 spectral range on a Nicolet Magna 860 ESP FT-IR spectrometer. Spectral acquisition conditions were 2 cm-1 digital resolution, 64 background scans (KBr only) and 64 sample (2% sample mixed with KBr) scans.

It will be appreciated that the resolution of DRIFT spectra may be influenced by the particle size of the sample being examined. The spectrum for Form B shown hereinafter was obtained with a sample which had been crushed to a fine powder. Repeated samples, or those with an alternative sample preparation may give DRIFT spectra which vary in resolution, although the peak position frequency therein will be unchanged.

Form B may also be characterised by other analytical techniques known in the art.

Typically Form B is obtained in a hydrated form with, for example, a water content of about 9-10% w/w, for example about 9% w/w.

Form B may be crystallised from a saturated solution of the Agent in aqueous [(E)-7-[4-(4-fluorophenyl)-6-isopropyl-2-[methyl(methylsulfonyl)amino]pyrimidin-5-yl](3R,5S)-3,5-dihydroxyhept-6-enoic acid] sodium salt (hereinafter referred to as 'Sodium Salt'). Suitably the amorphous form of the Agent is used as starting material and may be obtained, for example, as described in EPA 521471. The sodium salt may be prepared as described in WO 00/49014 and in Example 1 hereinafter.

Therefore in a further aspect of the present invention is provided a process for the manufacture of a crystalline hydrated form of a compound of formula (I) which comprises forming crystals from a saturated solution of compound of formula (I) in aqueous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] sodium salt.

A further aspect of the present invention provides a process for the manufacture of a crystalline hydrated form of a compound of formula (I) which comprises forming crystals from a saturated solution of the amorphous form of the compound of formula (I) in aqueous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] sodium salt.

Saturation of the sodium salt solution with the Agent means addition of, for example the amorphous form to the sodium salt solution until the solution is saturated with respect to the amorphous form. Further amorphous form is added to maintain the saturation once crystallisation of Form B has started.

The process of the invention is conveniently carried out between 20 and 45° C., more conveniently between 30 and 45° C., even more conveniently between 37 and 43° C., and preferably at about 40° C.

Form B may also be formed by seeding an aqueous solution or slurry of the amorphous form of the Agent, or by prolonged stirring of a solution of the amorphous form.

The utility of the compound of the invention may be demonstrated by standard tests and clinical studies, including those described in EPA 521471.

According to a further feature of the invention is a method of treating a disease condition wherein inhibition of HMG CoA reductase is beneficial which comprises administering to a warm-blooded mammal an effective amount of Form B of the Agent. The invention also relates to the use of Form B in the manufacture of a medicament for use in a disease condition.

The compound of the invention may be administered to a warm-blooded animal, particularly a human, in need thereof for treatment of a disease in which HMG CoA reductase is implicated, in the form of a conventional pharmaceutical composition. Therefore in another aspect of the invention, there is provided a pharmaceutical composition comprising Form B in admixture with a pharmaceutically acceptable carrier.

Such compositions may be administered in standard manner for the disease condition that it is desired to treat, for example by oral, topical, parenteral, buccal, nasal, vaginal or rectal administration or by inhalation. For these purposes the Agent may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solution or suspensions or sterile emulsions. A preferred route of administration is oral. The Agent will be administered to humans at a daily dose in, for example, the ranges set out in EPA 521471. The daily doses may be given in divided doses as necessary, the precise amount of the Agent received and the route of administration depending on the weight, age and sex of the patient being treated and on the particular disease condition being treated according to principles known in the art.

According to a further feature of the invention, there is provided a process for the manufacture of a pharmaceutical composition containing Form B as active ingredient, which comprises admixing Form B together with a pharmaceutically acceptable carrier.

It will be appreciated that the process described in WO2004/014872, for precipitation of the amorphous form of the Agent from a (substantially) aqueous solution of a different salt form, will generally lead to a proportion of residual Agent in waste solutions such as the mother liquors remaining after the precipitated Agent has been filtered off. Even a very small proportion of such residue may represent significant financial loss if the process is carried out repeatedly on a commercial manufacturing scale. Any reduction in such residue also potentially provides environmental benefits, reducing the amount of treatment that effluent requires before it can be disposed of.

We have found that this loss may be avoided by treatment of said waste solutions (such as mother liquors) such that the residue Agent may be isolated as Form B and then re-treated to form the desired amorphous form. Thus Form B has value as a processing aid for isolation of the amorphous form of the Agent. This aspect of the invention is illustrated in Example 3.

Therefore in a further aspect of the invention, there is provided a process for formation of amorphous bis[(E)-7-[4-(4-fluorophenyl)-6-isopropyl-2-[methyl(methylsulfonyl) amino]pyrimidin-5-yl](3R,5S)-3,5-dihydroxyhept-6-enoic acid] calcium salt comprising isolation of Form B as hereinbefore defined from a solution and subsequent conversion to the amorphous form.

In a further aspect, there is provided a process for formation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt comprising mixing a solution containing [(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt with a slurry of Form B in water, isolation of Form B and subsequent conversion of the isolated form B to the amorphous form, wherein Form B is as hereinbefore defined.

The process for isolation of form B is conveniently carried out between 20 and 45° C., more conveniently between 30 and 45° C., even more conveniently between 37 and 43° C., and preferably at about 40° C.

The solution containing [(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt is conveniently a waste solution such as a mother liquor solution from a process for formation and isolation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt from the corresponding sodium salt and calcium chloride. It will be appreciated that this waste solution will generally contain residual sodium chloride and potentially impurities arising from earlier stages in the synthetic process. The Form β isolated from this process is of high purity, for example >90% on dry weight basis, preferably >95%, more preferably >99%.

The quantity of Agent in the slurry of form B is conveniently approximately 15 mol % of that contained in the waste solution. The slurry and the waste solution are conveniently at a concentration of approximately 7 mg/ml.

In a further aspect of the invention, there is provided the use of Form B (as hereinbefore defined) as a processing aid for isolation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

In a further aspect of the invention, there is provided the use of Form B (as hereinbefore defined) as a processing aid for recovery of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt from waste solutions.

In a further aspect of the invention, there is provided the use of Form B (as hereinbefore defined) as an intermediate in the a manufacture of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

Under certain circumstances the Agent may exist in a crystalline form related to Form B which generally possesses long-range order, but only limited short-range order, and which generally has a lower water content than Form B. This form, related to Form B is hereinafter referred to as Form B-1. An XRD trace of Form B-1 is shown in Example 2A.

Form B-1 is produced by the removal of water from the crystal lattice of Form B. Upon dehydration, the long-range structure of Form B is retained in Form B-1, but Form B-1 has only limited short-range order. Form B-1 may be formed by heating a sample of Form B to 60° C. or by storing a sample of Form B at 0% Relative Humidity (RH) using equipment such as a DVS (Dynamic Vapour Sorption) instrument, for example a Surface Measurement Systems DVS_1, as described in Example 2. Form B-1 may be converted back to Form B by appropriate exposure to water, for example by slurrying in water. As illustrated in Example 2, Form B-1 demonstrates a distinct XRD pattern in comparison to that of Form B. The XRD pattern of Form B-1 may be determined by the method hereinbefore described for Form B.

Therefore in another aspect there is provided a 'dehydrated hydrate' form of the Agent having an X-ray powder diffraction pattern with peaks at 2-theta (2θ)=4.4, 7.7, 9.0 and 20.7 at 0% RH. In a further aspect there is provided a 'dehydrated hydrate' of the Agent having an X-ray powder diffraction pattern with peaks at 2-theta (2θ)=4.4, 9.0 and 20.7 at 0% RH. In a further aspect there is provided a 'dehydrated hydrate' of the Agent having an X-ray powder diffraction pattern substantially as shown in FIG. 2A.

Exposure of Form B-1 to humidities above 0% RH allows water to re-enter the crystal lattice to a level dictated by the RH of the environment. However, water vapour does not easily reorder the structure to reproduce Form B, hence the material continues to lack short-range order and water is easily lost on lowering the relative humidity. The absorption and desorption of water may lead to small shifts in the XRD peaks.

A DRIFT spectrum of Form B-1 is included in Example 2 hereinafter. The experimental conditions were as described hereinbefore for Form B, except that the sample was gently crushed.

The invention will now be illustrated by the following Examples.

Example 1

Aqueous sodium hydroxide (8% w/w, 27.2 ml) was added to a stirred mixture of [(E)-7-[4-(4-fluorophenyl)-6-isopropyl-2-[methyl(methylsulfonyl)amino]pyrimidin-5-yl](3R,5S)-3,5-dihydroxyhept-6-enoic acid] methylamine salt (30 g) in purified water (234 ml) at 20° C. and the mixture was stirred for 15 min. The mixture may be filtered if necessary to remove insoluble material. The mixture was concentrated under reduced pressure at <40° C. until 142 ml of distillate collected. Water (90 ml) was added and the mixture again concentrated under reduced pressure at <40° C. until 90 ml of distillate collected. The resulting solution of [(E)-7-[4-(4-fluorophenyl)-6-isopropyl-2-[methyl(methylsulfonyl)amino]pyrimidin-5-yl](3R,5S)-3,5-dihydroxyhept-6-enoic acid] sodium salt was made up to a volume of 295 ml with water (125 ml) at 40° C. and bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt (8 g) (amorphous) was added. After stirring for approximately 20 hours a gel was observed. After a further 7 hours of stirring at 40° C. crystallisation was observed (confirmed by optical microscopy). Further bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt (amorphous, 17 g) and water (100 ml) were added. The thick slurry was stirred for a further 16 hours at 40° C. after which time the material appeared totally crystalline by optical microscopy. The crystalline material was cooled to 20° C., isolated, washed with water (3×90 ml) and dried under vacuum at approximately 35° C. to give 23 g (95% yield based on 96% strength input amorphous calcium salt).

Water content 9.1% w/w $^1$H NMR (400 MHz, DMSO-D6) δ ppm*: 1.2 (d, 3H) 1.2 (d, 3H) 1.3 (m, 1H) 1.5 (m, 1H) 2.0 (dd, 1H) 2.1 (dd, 1H) 3.4 (s, 3H) 3.5 (s, 3H) 3.8 (m, 1H) 4.2 (q, 1H) 5.5 (dd, 5.4 Hz, 1H) 6.5 (dd, 1H) 7.3 (m, 2H) 7.7 (m, 2H)

*Chemical shifts were measured in parts per million relative to tetramethylsilane. Peak multiplicities are shown as follows: s, singlet; d, doublet; t, triplet; m, multiplet.

X-Ray Powder Diffraction (XRD):

The Form B sample was crushed to a fine powder before being homogeneously mixed with KBr. Other experimental conditions have been described hereinbefore.

Example 2

A sample of Form B (approximately 6 mg) was dispensed into a glass sample pan and suspended from the balance of an SMS Dynamic Vapour Sorption (DVS) instrument. The DVS instrument was then used to hold at 0% RH, 30° C., overnight (after this time period the change in sample mass was <0.002%/min over at least an hour). The sample was then analysed immediately by XRD. The sample was exposed for 0.40 sec per 0.0357° 2θ over the range 3° to 30° 2θ in continuous scan, theta-theta mode.

FIG. 2A is an example XRD trace of a sample of Form B-1 which has been stored at 0% RH. It will be appreciated that variations in the water content of the sample of Form B-1 will cause variations in the precise 2θ values described below, such variations in water content resulting for example by the conditions of storage of Form B-1.

FIG. 3 is a comparison of the XRD traces of Forms B and B-1.

Example 3

Example of Mother Liquor Recovery Process

Bis[(E)-7-[4-(4-fluorophenyl)-6-isopropyl-2-[methyl (methylsulfonyl)amino]pyrimidin-5-yl](3R,5S)-3,5-dihydroxyhept-6-enoic acid] calcium salt mother liquors (6000 ml @ approximately 7/mg/ml) and a slurry of Form B (900 ml @0.7% w/v in water) were mixed together at 40° C. over 80 minutes. The slurry was then held for a further 6 hours with stirring at 40° C. The mixture was then cooled to 5° C. and held at that temperature with stirring for a further 2 hours. Bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt Form B was isolated and dried under vacuum at 22° C. under nitrogen. Approximately 75% of the available Bis[(E)-7-[4-(4-fluorophenyl)-6-isopropyl-2-methyl(methylsulfonyl)amino]pyrimidin-5-yl](3R,5S)-3,5-dihydroxyhept-6-enoic acid] calcium salt in the mother liquors and washes was recovered as isolated crystalline Form B.

The Form B may be converted to amorphous Agent as follows:

A suspension of crystalline Form B (17.32 g) in acetonitrile (148 ml) was treated with water (70 ml) to form a solution at 20° C. Sodium chloride (18.8 g) was added to the solution and the pH is adjusted to 2.8-3.4 at 0° C. with aqueous hydrochloric acid and brine solution. The product [(E)-7-[4-(4-fluorophenyl)-6-isopropyl-2-[methyl(methylsulfonyl)amino]pyrimidin-5-yl](3R,5S)-3,5-dihydroxyhept-6-enoic acid was extracted (or partitioned) into the acetonitrile phase then diluted with water (72 ml). The pH was adjusted to pH 10.5 with sodium hydroxide. Water was then added so that the total volume of water and sodium hydroxide added was equal to 100 ml. The mixture is washed with toluene (125 ml). After removal of the acetonitrile from the aqueous phase by vacuum distillation, calcium chloride solution (3.05 g in approx 30 ml water) was added to the residue at 40° C. over 20 minutes. The amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt was isolated by filtration at 20° C., and washed with water, before drying under vacuum to give the amorphous agent (14.2 g, 82%).

Reference Example 1

For reference purposes, FIG. 4 shows the XRD pattern for Form A, as described in WO 00/42024.

The invention claimed is:

1. A crystalline hydrated form of the compound bis[(E)-7-[4-(4fluorophenyl)-6-isopropyl-2-[methyl(methylsulfonyl) amino]pyrimidin-5-yl](3R,5S)-3,5-dihydroxyhept-6-enoic acid] calcium salt of formula I

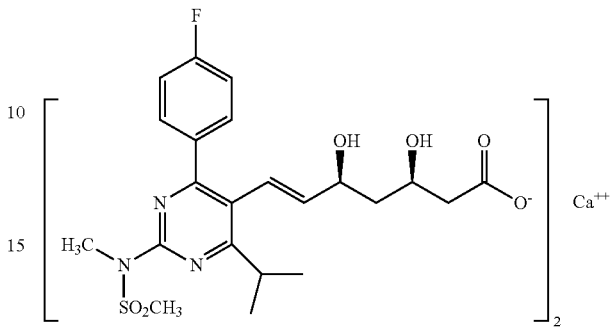

having an X-ray powder diffraction pattern with peaks at 2-theta (2θ)=8.8, 13.1 and 21.5°.

2. The crystalline hydrated form as claimed in claim 1 with an X-ray powder diffraction pattern with peaks at 2-theta (2θ)=4.3, 8.8, 13.1, 13.7, 21.5, 22.8 and 28.9°.

3. The crystalline hydrated form as claimed in claim 1 with an X-ray powder diffraction pattern with peaks at 2-theta (2θ)=4.3, 8.8, 13.1, 13.7, 15.2, 15.8, 17.5, 21.5, 21.9, 22.8, 24.5 and 28.9°.

4. The crystalline hydrated form as claimed in claim 3 which contains about 9-10% water.

5. The crystalline hydrated form as claimed in claim 1 having an X-ray powder diffraction pattern substantially as shown in FIG. 1.

6. A crystalline form of the compound bis[(E)-7-[4-(4-fluorophenyl)-6-isopropyl-2-[methyl(methylsulfonyl) amino]pyrimidin-5-yl](3R,5S)-3,5-dihydroxyhept-6-enoic acid] calcium salt of formula I

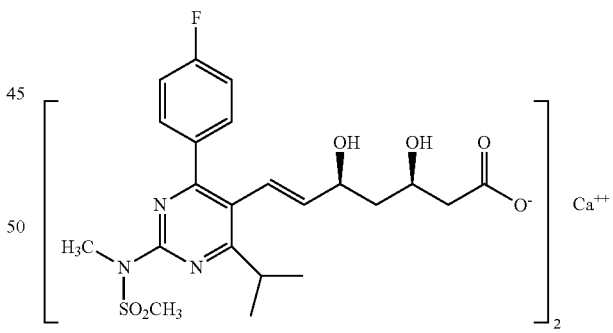

having an X-ray powder diffraction pattern with peaks at 2-theta (2θ)=4.4, 7.7, 9.0 and 20.7°.

7. The crystalline form as claimed in claim 6 having an X-ray powder diffraction pattern substantially as shown in FIG. 2.

8. A pharmaceutical composition comprising the crystalline form as claimed in claim 1 or claim 6 and a pharmaceutically acceptable carrier.

9. A process for formation of amorphous bis[(E)-7-[4-(4-fluorophenyl)-6-isopropyl-2-[methyl(methylsulfonyl) amino]pyrimidin-5-yl](3R,5S)-3,5-dihydroxyhept-6-enoic acid] calcium salt comprising isolating from a solution the crystalline form as claimed in claim 1 or claim 6; and subsequently converting the crystalline form to an amorphous form.

10. The process as claimed in claim 9 comprising mixing a solution containing [(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt with a slurry of the crystalline form as claimed in claim 1 or claim 6 in water;

isolating crystals of the crystalline form; and subsequently converting the isolated crystals to the amorphous form.

11. The process as claimed in claim 10 wherein the solution containing the [(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt is a waste solution.

12. The process as claimed in claim 10 wherein the mixing is carried out between 37 and 43° C.

13. A process for the manufacture of the crystalline form as claimed in claim 1 or claim 6 which comprises forming crystals from a saturated solution of a compound of formula (I) in aqueous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] sodium salt.

14. A process for the manufacture of the crystalline form as claimed in claim 1 or claim 6 which comprises seeding an aqueous solution or slurry of a compound of formula I.

15. A process for the manufacture of the crystalline form as claimed in claim 1 or claim 6 which comprises prolonged stirring of a solution of an amorphous form of a compound of formula I.

16. A process for the manufacture of the pharmaceutical composition as claimed in claim 8 which comprises admixing the crystalline form together with a pharmaceutically acceptable carrier.

17. A method of treating hyperlipidemia, hypercholesterolemia or atherosclerosis which comprises administering to a warm-blooded mammal in need thereof an effective amount of the crystalline form as claimed in claim 1 or claim 6.

18. The process as claimed in claim 11, wherein the waste solution is a mother liquor solution from a process for formation and isolation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt from the corresponding sodium salt and calcium chloride.

* * * * *